(12) United States Patent
Thym et al.

(10) Patent No.: US 9,101,307 B2
(45) Date of Patent: Aug. 11, 2015

(54) MEDICAL SYSTEM AND METHOD FOR OPERATING A MEDICAL SYSTEM

(75) Inventors: Detlef Thym, Mannheim (DE); Robert Lorenz, Worms (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 333 days.

(21) Appl. No.: 13/445,607

(22) Filed: Apr. 12, 2012

(65) Prior Publication Data

US 2012/0262274 A1 Oct. 18, 2012

(30) Foreign Application Priority Data

Apr. 15, 2011 (EP) ..................................... 11162641

(51) Int. Cl.
| | |
|---|---|
| *G06K 7/01* | (2006.01) |
| *A61B 5/151* | (2006.01) |
| *A61B 5/145* | (2006.01) |
| *A61B 19/00* | (2006.01) |

(52) U.S. Cl.
CPC ............. *A61B 5/14532* (2013.01); *A61B 19/44* (2013.01); *A61B 2019/448* (2013.01); *A61B 2019/4873* (2013.01); *A61B 2560/029* (2013.01); *A61B 2562/0247* (2013.01)

(58) Field of Classification Search
CPC ................. G07C 9/00182; G07C 2009/00793; B60R 25/24; A61B 5/14532; A61B 19/44; A61B 2019/4873; A61B 2562/0247; A61B 2019/448; A61B 2560/029
USPC .............. 340/5.1, 5.2, 539.1, 539.11, 539.12; 600/583
See application file for complete search history.

(56) References Cited

U.S. PATENT DOCUMENTS

| | | | |
|---|---|---|---|
| 5,989,917 A | 11/1999 | McAleer et al. | |
| 7,178,416 B2 | 2/2007 | Whelan et al. | |
| 7,198,190 B2 | 4/2007 | Juhan et al. | |
| 8,085,132 B2 * | 12/2011 | Allen et al. | 340/10.2 |
| 8,517,930 B2 * | 8/2013 | Sauer et al. | 600/184 |
| 2005/0003122 A1 | 1/2005 | Debraal et al. | |
| 2006/0109118 A1 * | 5/2006 | Pelo et al. | 340/572.1 |
| 2006/0265246 A1 * | 11/2006 | Hoag | 705/2 |

(Continued)

FOREIGN PATENT DOCUMENTS

| | | |
|---|---|---|
| DE | 69816045 T2 | 1/2004 |
| WO | 2007/136902 A2 | 11/2007 |

(Continued)

*Primary Examiner* — Jennifer Mehmood
*Assistant Examiner* — Yong Hang Jiang
(74) *Attorney, Agent, or Firm* — Roche Diagnostics Operations, Inc.

(57) ABSTRACT

A medical system and method to operating the medical system is presented. A patient storage element is assigned to a patient comprising identification information identifying the patient. A medical device has a contaminating patient application. A medical device storage element on the medical device comprises use information. A clearing device receives the identification information from the patient storage element and the use information from the medical device storage element and analyzes the use information. If in analyzing the use information it is found that application of the medical device to the patient is allowed, a clearance signal is outputted. If in analyzing the use information it is found that application of the medical device to the patient is not allowed, the identification information is analyzed. If in analyzing the identification information it is found that application of the medical device to the patient is allowed, a clearance signal is outputted.

13 Claims, 3 Drawing Sheets

(56) References Cited

U.S. PATENT DOCUMENTS

| | | |
|---|---|---|
| 2008/0007409 A1* | 1/2008 | Ferry et al. .................. 340/572.1 |
| 2009/0119024 A1 | 5/2009 | Pritchard et al. |
| 2010/0145721 A1* | 6/2010 | Deshays ............................ 705/2 |
| 2010/0256990 A1 | 10/2010 | Horiguchi et al. |
| 2010/0327057 A1 | 12/2010 | Medina et al. |
| 2011/0112384 A1 | 5/2011 | Eisenhardt et al. |

FOREIGN PATENT DOCUMENTS

| | | |
|---|---|---|
| WO | 2008/034913 A2 | 3/2008 |
| WO | 2008/061313 A1 | 5/2008 |
| WO | 2009/053437 A1 | 4/2009 |

* cited by examiner

MEDICAL SYSTEM AND METHOD FOR OPERATING A MEDICAL SYSTEM

CROSS-REFERENCE TO RELATED APPLICATIONS

This application is a based on and claims priority to EP 11162641.2. filed Apr. 15, 2011, which is hereby incorporated by reference.

BACKGROUND

The present disclosure generally relates to a medical system and a method for operating a medical system.

Medical systems are typically used to perform a specific treatment and/or diagnostic step on patients. A large proportion of medical systems can be contaminated in the course of such treatment, or diagnostic step, in that at least parts of the medical system come directly, or indirectly, into contact with the patient's body, in particular with bodily fluids. This contamination can be caused by direct contact between parts of the medical system and the body of the patient. A contamination can however also arise in that a sample of bodily fluids taken from the body is placed in a test, or analysis, device at which point this test, or analysis, device can be contaminated with the bodily fluid. Such devices can include, for example, blood sugar testing devices where the blood sugar value is determined from patient blood samples. In connection with the extraction of blood samples, it is known that lancing devices can be used to pierce the skin of the patient for the purpose of taking a blood sample.

Therefore, there is a need to provide improved technologies for a medical system and a method for operating a medical system which will reduce the risk of infection for the user.

SUMMARY

According to the present disclosure, a medical system is presented. The medical system comprises a patient storage element that is assigned to a patient by identification information identifying the patient, a medical device having a contaminating patient application, a medical device storage element provided on the medical device and comprising use information and a clearing device that receives the identification information from the patient storage element and the use information from the medical device storage element and analyzes the use information. If in analyzing the use information it is found that application of the medical device to the patient is allowed, a clearance signal is outputted. If in analyzing the use information it is found that application of the medical device to the patient is not allowed, the identification information is analyzed. If in analyzing the identification information it is found that application of the medical device to the patient is allowed, a clearance signal is outputted.

Accordingly, it is a feature of the embodiments of the present disclosure to provide improved technologies for a medical system and a method for operating a medical system which will reduce the risk of infection for the user. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
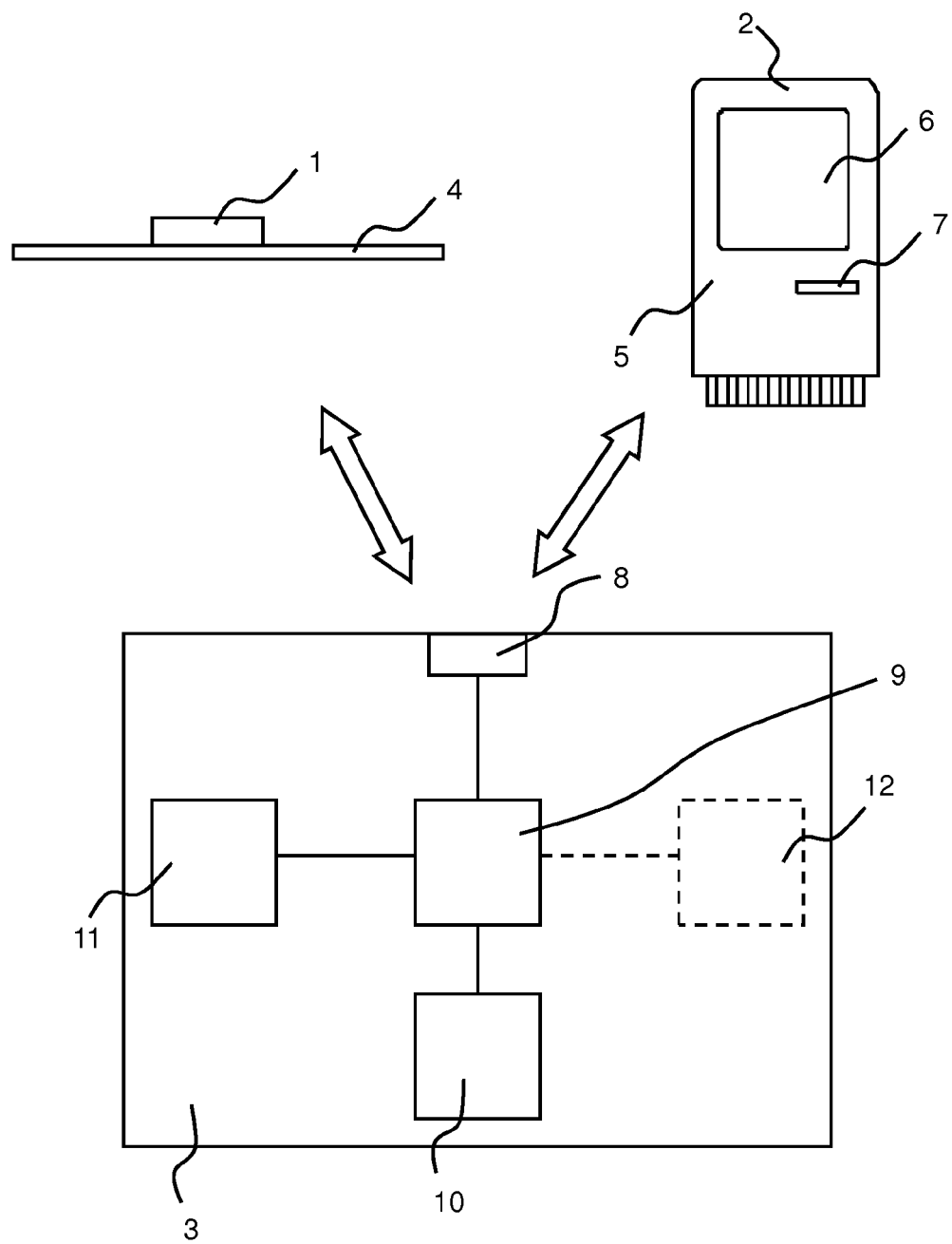
FIG. 1 illustrates a schematic representation of a medical system comprising a medical device according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A technology can be provided by which a compulsory analysis can be undertaken prior to the use of a medical device with the help of a clearing device that determines whether the medical device is prepared for a current use for the patient. For this analysis, use information can be received from the medical device storage element by the clearing device. Also, identification information can be received from the patient storage element by the clearing device. In a first step, the use information received from the medical device storage element can be evaluated. If this evaluation shows, for example, that the medical device has previously been disinfected, the application for the patient can be cleared. Only when the analysis reveals that application on the patient is allowed, a clearance signal can be outputted by the clearing device. The clearance can occur without detailed analysis if the use information shows that the device is a new device that has not been used.

If in analyzing the use information it is found that application of the medical device to the patient is not allowed, e.g. because of prior use of the device, the identification information received from the patient storage element can be analyzed. If it is found that application of the medical device to the patient is allowed, a clearance signal can be outputted. If, in an exemplary embodiment, a prior use of the medical device for a patient is indicated by the use information, the clearance can finally occur if the respective patient in question is the one identified by the identification information.

The term "patient storage element" can refer to a data storage element affixed to a patient's body or unequivocally assigned to a patient. Information stored on the data storage element can be read by a contactless reading method such as, for example, an optical and/or a non-optical reading or scanning procedure.

The term "medical device storage element" can refer to a data storage element affixed or unequivocally assigned to a reusable medical device or instrument. Information stored on the data storage element can be read out by a contactless reading method, such as, for example, an optical and/or a non-optical reading or scanning procedure.

The term "a contaminating patient application" can refer to an application on the patient device, wherein the device can have a potential contact, or the risk of a contact, with a bodily fluid, especially blood, and thereby can have the risk of cross-contamination and/or the risk of a potential blood-borne infection, e.g. HIV or hepatitis B.

The clearance signal may be a signal that indicates to the user that use of the device is allowed. Such signal may be outputted by a signalling component of the clearance device itself. For example, an optical and/or an acoustic signal may be outputted. Also, as an alternative or in addition, such signalling to the user may be provided by the medical device. In addition or as an alternative, the clearing signal may comprise a signal component provided to the medical device for clearing operation of a component or a unit of the medical device or the medical device as whole, e.g. by clearing a blocking of the component and/or the medical device. In such case, the clearing signal, or its signal component, may also be referred to as component/unit or device control or operation clearing signal. In one embodiment, clearing of a device component/unit and/or the device as whole may occur without outputting a signal to the user. The user can learn that clearance has occurred by noticing usability of the medical device.

The clearance signal can comprise acoustic and/or optical signals. Alternatively or in addition, a vibration signal could be produced as is known in the context of handheld devices such as mobile telephones. In this way, the user can be signalled prior to using the medical device as to whether the current use of the medical device is allowed for patients or not. If, for example, the last use was for another patient, whereby the use information on the storage element of the medical device storage element identifies another patient, the clearance signal will not be emitted. Instead, a warning signal may be outputted.

In one embodiment, the patient storage element can be an electronic storage element loaded with electronic identification about the patient. The patient storage element may be worn on the body of the patient. In this way, information can be available on the patient if a use of the medical device is planned. The data on the patient storage element and on the medical device storage element can be analyzed with the help of the clearing device by the comparison of data, for example. In another embodiment, the patient storage element can be a storage element which can be read optically. For example, a storage element with a bar code and/or a 2D bar code and/or a hologram may be provided. In this case, the clearing device can have a reader module to read the optical information.

Especially with respect to the medical device storage element, the medical device storage element can be a storage element accessible by non-optical read and/or write operations such as, for example, RFID technology or electronic data memory devices. In one embodiment, the medical device storage element, and optionally also the patient storage element, may be a storage element containing electronic information or data.

If both the patient storage element and the medical device storage element contain electronic information, or data, a medical system can comprise a patient storage element, a medical device, a medical device storage element and a clearing device. The patient storage element can be assigned to a patient by comprising electronic identification data identifying the patient. The medical device can have a contaminating patient application. The medical device storage element can be on the medical device and can comprise electronic use information. The clearing device can receive the identification information from the patient storage element and the use information from the medical device storage element and can analyze the use information. If in analyzing the use information it is found that application of the medical device to the patient is allowed, a clearance signal can be outputted. If in analyzing the use information it is found that application of the medical device to the patient is not allowed, the identification information can be analyzed. If in analyzing the identification information it is found that application of the medical device to the patient is allowed, the clearance signal can be outputted.

If the clearing device signals a clearance, the medical device may be used by the patient. In the course of such use or in the course of a first use, in one embodiment, information about the patient can be automatically stored on the medical device storage element which identifies the patient for which the use then currently occurs. This can, for example, be provided in that electronic identification data stored on the patient storage element can be transferred in full, or in part, to the medical device storage element. Alternatively or additionally, with the help of the clearing device, information on the prior usages of the medical device for the patient can also be stored on the medical device storage element. Thereby, the electronically stored information in the medical device storage element can also comprise further electronic identification data which can then be analyzed by the clearing device prior to the next use of the medical device.

A medical device can be a device having a contaminating medical patient application based on direct contact with the patient or based on indirect contact such as, for example, through a patient bodily fluid sample being analyzed or determined with the help of the medical device. The latter can be, for example, a blood sugar testing device.

In another embodiment, the use information can comprise at least one kind of information selected from the following group: further identification information, disinfection information, and non-use information. The further identification information may be further electronic identification data. In a one embodiment, disinfection information can be stored on the medical device storage element. The disinfection information may be on the medical device storage element in addition, or alternatively, to further identification information. In case of the clearing device, the clearing signal may be outputted immediately if the disinfection information is detected on the medical device storage element. This is because the medical device is ready for use in view of the disinfection procedure having been done before. No further analysis of the identification information is needed because the identity of the patient does not matter since the device has been disinfected. Therefore, analysis of the identification information can be optional in such situations. Also, information on the medical device storage element indicating that the medical device has not been in use for contaminating patient application at all may be present. Such information may be referred to as non-use information. The non-use information, for example, may indicate that this is a new medical device that has not been used previously. In such a case, also, the clearing signal may be outputted without further data analysis, since there is no risk of infection due to prior use with some other patient. Again, analysis of the electronic identification data may be optional in such situations.

In a yet another embodiment, the clearing device can at least be partially implemented as an integrated device together with either the patient storage element or the medical device storage element. In this embodiment, the clearing device can be implemented with its components, fully, or in part, with the patient storage element and/or the medical device storage element. The clearing device may also be referred to as a clearing module or clearing component. In this way, it is possible for the clearing device to be integrated into the medical device so that a type of combination device can be created. In one embodiment, the clearing device can be an integral part of a blood sugar testing device in which a blood sugar or glucose value is determined from a blood sample. The blood sugar testing device can in turn, in this or another design, be part of a system which can also comprise a lancing device and/or an insulin pen (i.e., an apparatus for administering insulin). The clearing device can also be formed in a device, or system unit, with the patient storage element. In this way, a unit can be worn on the body of the patient such that the unit can be attached to a wrist or ankle band which can be removably attached to the body, for example, by a suitable hook and loop fastening.

In still a further embodiment, at least one of the patient storage element and the medical device storage element can be a RFID storage element. Such storage elements can form transponders which are known in various embodiments. The data transfer can occur in RFID technology via radio waves or via wireless data communications.

In another embodiment, at least one of the patient storage element and the medical device storage element can be a passive storage element. The patient storage element can be a read only memory (ROM). The medical device storage element can be a read and write memory. In this way, it can be possible for the medical device storage element to be written over with electronic data, for instance, after being disinfected or applied to a patient.

According to one embodiment, at least one of the patient storage element and the medical device storage element can be an active storage element. An active storage element can be connected to its own energy source. Therefore, the active storage element can actively transmit stored electronic data. For example, the patient storage element may actively send out the electronic identification data identifying the patient to the clearing device. In addition or alternatively, the medical device storage element may be implemented as an active storage element being able to actively transmit the electronic use information to the clearing device. Such active data transmission may be started in at least one of the storage elements in response to detection of the clearing device in the vicinity of the location of one of the storage elements. Also, an active transmission of the electronic data identifying the patient to the medical device storage element may be started in response to detection of the medical device storage element in the vicinity of the location of the patient storage element. Thereby, electronic information about (potential) application of the medical device to the patient identified by the electronic identification data on the patient storage element can be automatically transferred to the medical device storage element.

In still a further embodiment, the patient storage element can be on a patient attachment element. The patient attachment element may be a disposable article. The patient storage element may be detachably or non-detachably connected to the patient attachment element and can be constructed in a way that it can be removed without any destruction, or alternatively only through destruction of the function of the disposable storage element. For example, the patient attachment element can be a wrist or ankle band detachably connected to the respective place on the body. An alternative embodiment may be that the patient storage element is attached to the body using an adhesive, for example, on a fingernail or toenail, on the hair or any other suitable body part. In one embodiment, the adhesive used on a fingernail or toenail can be, for example, superglue. The wrist or ankle band can have any suitable form. In this way, for example, plastic materials may be used whose ends can be detachably, or non-detachably, connected to one another. A non-detachable connection can be, for example, heat sealing, thermal riveting or irreversible snap joint. In one embodiment, the patient storage element, for example a RFID chip, can be implanted under the skin.

In one embodiment, the medical device storage element can be a disposable article detachably applied to the medical device. The detachable connection of the storage element to the medical device, for example, can make it possible that the medical device storage element can be replaced by a new disposable storage element after a disinfection procedure. A detachable connection can be achieved through the use of any suitable adhesive. In one embodiment, the medical device storage element can be a label with an integrated RFID and an adhesive for attachment. Such a label, for example, can be constructed so that it can be removed without any destruction, or alternatively only through destruction of the function of the disposable storage element. A mechanical connection such as, for example, a reversible or irreversible snap joint, can also be used. Alternatively, the medical device storage element can be non-detachably connected to the medical device. Such a connection can, for example, be achieved through a plastic band or a shrink film so that the medical device storage element is only removable through the destruction of the attachment and optionally through the destruction of the function of the disposable storage element. Connection with super glue can also be provided. In one embodiment, the medical device storage element can be integrated into the housing of the medical device.

As an alternative to the replacement of the medical device storage element after disinfection, the medical device storage element can be electronically reset so that data related to the use for the patient stored thereon is deleted. The medical device can thus be ready for use on the same patient for which the medical device was previously used or another patient. If such reset storage is detected with the help of the clearing device, a clearing signal can be outputted.

In another embodiment, at least one of the patient storage element and the medical device storage element can be functionally connected to a motion sensor. The functionally or operationally coupling of the respective storage element to a motion sensor can enable an operation mode in which, for example, the sending and/or reception of electronic data by the storage element can be automatically initiated if moved. In this way, for instance, in connection with the medical device storage element, this element can automatically send the electronic use information if motion is detected by a respective motion sensor. The data transmitted can then be received by the clearing device. In a similar way, this can be provided for the patient storage element. Alternatively or in addition, the clearing device can have a motion sensor so that a type of use for the clearing device is possible for which the clearing device can be activated through detected motion in order to receive data from storage elements in the vicinity whereby a clearing process may be automatically initiated.

According to one embodiment, the clearing device can comprise a detection element and can start an operation mode in which the identification information and the use information can be collected automatically by the clearing device from the patient storage element and the medical device storage element, respectively, if at least one of the patient storage element and the medical device storage element is detected by the detection element as being located in the vicinity of the medical device. In this mode of operation, the electronic identification information and the electronic use information can be collected, or gathered, by the medical device without waiting for user input to initiate such data collection. For example, the automatic data collection may be started in response to a signal received from a motion sensor.

In still a further embodiment, the clearing device can be connected to an operation module of the medical device. The clearing device can, if in analyzing it is found that application of the medical device to the patient is allowed, output the clearance signal with an operation clearing signal provided to the operation module for clearing use of an operation function of the medical device. In this embodiment the clearing signal can be provided with an operation clearing signal which clears operation of a function and/or a functional element of the medical device. In case there is no allowed application to the patient, e.g. no patient identity, a locking signal may be provided which will lock the respective operation function against use. For example, in a medical device being provided as a testing, or analyzing, device for a bodily fluid such operation function may be any required preparation, or functional, step prior to application of bodily fluid sample. Such a required preparation, or functional, step can be, for example, providing a required testing element (such as a test strip), clearing an unused testing element for sample application or a display message. In case the locking signal is dispatched, such operation function can be blocked. In another embodiment, the medical device may be a puncturing device for puncturing the skin of the patient. If the locking signal is dispatched, the puncturing function can be blocked. In another embodiment, the medical device may be provided as an insulin pen for injecting insulin. If a criterion for allowing use is lacking, e.g. identity of the patient identifying information, clearance of the cannula can be blocked by the locking signal. The aforementioned embodiments may be implemented by combining the medical device and the clearing device into an integrated device.

According to a further embodiment, the medical device can be a device, or a combination of devices, such as a lancing device for puncturing a patient skin, a sample taking device for taking a bodily fluid sample, a testing device for determining a bodily fluid, and/or a medical injection device for administering fluids parenterally (such as an insulin pen). The sample taking device, for example, may take a blood sample from the patient. In one embodiment, the testing device can determine a blood sugar value for a blood sample of the patient.

The embodiment of the patient storage element and/or the medical device storage element as an active storage element can provide for the active transmission of the electronic data by the storage element, in particular to the clearing device. Through the possible use of one or more motion sensors, method steps can be automatically initiated when motion is detected.

In one embodiment, an analysis may be performed with the help of the clearing device as to the usability for one patient of several components of a medical device and/or several medical devices. In this way, in connection with a blood sugar testing device, the analysis may be performed for a testing device and also a lancing device whereby both the testing device and the lancing device can both be provided with an allocated electronic storage element. In addition to or as an alternative to the analysis for the lancing device, an analysis for an insulin pen can be provided. In this context, in one embodiment, the clearing signal can only be outputted if usability is determined for several components of a medical device or several medical devices. In another case, the components of the medical device or devices can be blocked and/or a warning signal emitted. Such blocking may be implemented by actively blocking in case there is no clearance or by not clearing a blocking status which may be referred to as passive blocking. The implementations described can be used with only one medical device.

Referring initially to FIG. 1, FIG. 1 shows a schematic representation of a medical system comprising a patient storage element 1, a medical device 2, and a clearing device 3. The patient storage element 1 can be arranged on a fastening element 4 such as, for example, a tie strap, so that a patient can attach the patient storage element 1 to his body. The patient storage element 1 can have identification information such as, for example, electronic identification data, loaded onto it which can distinctly identify the patient, or user, who is wearing the patient storage element 1 on his body with the help of the fastening element 4. Any identification data can be stored on the patent storage element that is suitable for identifying the patient distinctly from other patients. In one embodiment, the patient storage element 1 can be a RFID transponder, i.e., a storage element with which data transfer by RFID technology may occur.

In one embodiment, the medical device 2 can be a blood sugar testing device with which the blood sugar value can be determined from a patient's extracted blood samples. A medical device storage element 7 can be arranged on the housing 5 of the medical device 2 below a display 6. The medical device storage element 7 can store electronic data and can also be an RFID transponder. Both the patient storage element 1 and the medical device storage element 7 can be read with a read-write-unit 8 of the clearing device 3. The electronic data received by the clearing device 3 can then be processed with a control unit 9. Depending on the processing, the control unit 9 can affect the output of signals via an output element 10 of the clearing device 3. Acoustic and/or optical signals can be output. The clearing device 3 can also output vibration signals. According to FIG. 1, the clearing device 3 can have a storage unit 11 to store electronic data. Further components can be provided in the clearing device 3 shown by the component 12 outlined with dotted lines.

Figure 2:
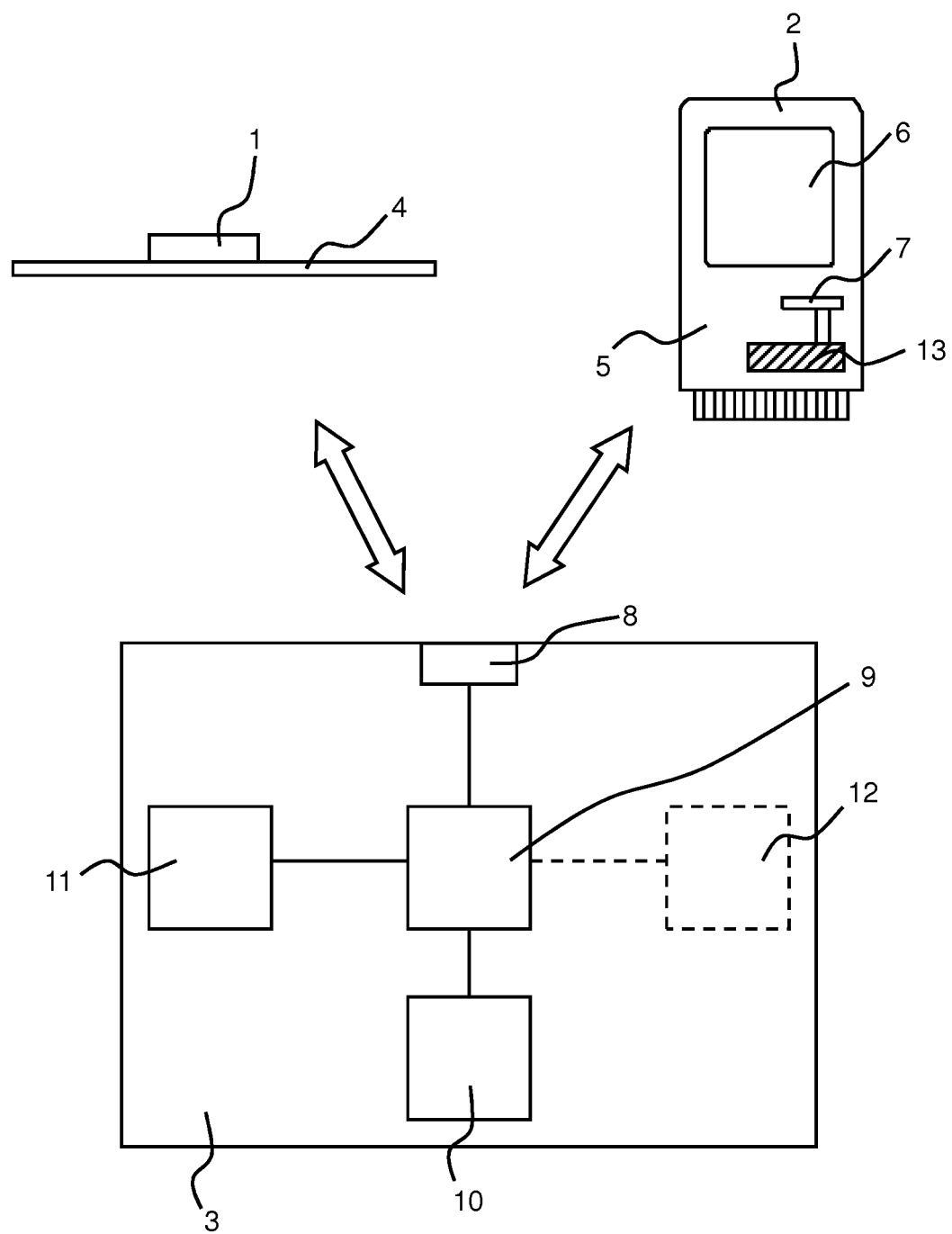
FIG. 2 illustrates a schematic representation of another medical system comprising a medical device which is provided with a motion sensor according to an embodiment of the present disclosure.

FIG. 2 shows a schematic representation of another medical system in which the medical device 2 additionally can comprise a motion sensor 13 connected to the medical device storage element 7. The motion sensor 13 can be functionally coupled to the medical device storage element 7. If the medical device storage element 7 is an active storage element, an operation mode can be provided in which electronic data stored in the medical device storage element 7 are automatically transmitted when a motion of the medical device 2 is detected by the motion sensor 13. Thereby, electronic data stored in the medical storage element 7 may be transferred from the medical device 2 to the clearing device 3 without receiving a user input either in the medical device 2 or the clearing device 3.

With the help of the medical systems in FIGS. 1 and 2, different methods of operation with different types of use can be provided. In one exemplary method for the operation of the medical system, the medical device 2 embodied as a blood sugar testing device is used to determine a blood sample of a patient who is wearing the patient storage element 1 and who is identifiable with the help of electronic identification data stored on the patient storage element 1. In the course of the blood sugar analysis, the physical proximity of the patient storage element 1 and the medical device 2 with attached medical device storage element 7 causes the partial or complete transfer of the electronic data identifying the patient from the patient storage element 1 to the medical device storage element 7. In this way, electronic information is stored on the medical device storage element 7 that the medical device 2 was used in a contaminating manner for the patient identifiable through the electronic identification data on the patient storage element 1.

If the medical device 2 is later to be used for a new blood sugar analysis, the electronic identification data on the patient storage element 1 and the electronic data on the medical device storage element 7 can be read and compared by the clearing device 3. If the electronic data in the patient storage element 1 and the medical device storage element 7 both identify the same patient, the clearing device 3 can subsequently output a clearance signal. For example, a green light could be illuminated. In addition or as an alternative, an acoustic signal can be outputted or text can be displayed. In this way, the user of the medical system can know that a renewed use of the medical device 2 is possible in connection with the patient who has been identified using the electronic identification data.

If it is determined during analysis of the electronic identification data in the clearing device 3 that the data read does not identify the same patient, a warning signal can be outputted. For example, a red light could flash. In addition or as an alternative, an acoustic warning signal can be outputted, a vibration warning signal can be outputted, or warning text could be displayed. Such a case could occur, for example, if the medical device 2 previously used for analyzing blood sugar is now to be used for another patient who is identified by the electronic identification data attributed to him. The output of a warning signal can help ensure that the contaminated medical device 2 is not used for the other patient.

This warning does not occur if the medical device 2 previously used has been disinfected or sterilized before the intended use of another patient. In this case, the data stored on the medical device storage element 7 for the previous use can be erased so that the medical device storage element 7 no longer contains the previous data. Then, when the clearing device 3 reads the medical device storage element and the patient storage element, clearance can be immediately given due to the lack of personal identification data on the medical device storage element 7 so that the medical device 2 may be used for the other patient.

In connection with the sterilization or disinfection process, the medical device storage element 7 can be replaced by a new storage element, for example, by removing the previously used storage element and affixing a new storage element. The new storage element can be free of personal identification data resulting in the output of a clearance signal when checked by the clearing device 3.

In another embodiment, in connection with a sterilization or disinfection process, the electronic data about the process can be saved on the medical device storage element 7. This information can then be read by the clearing device 3 in the analysis process. Ultimately, this data can show that the medical device 2 is available for use by another patient.

Figure 3:
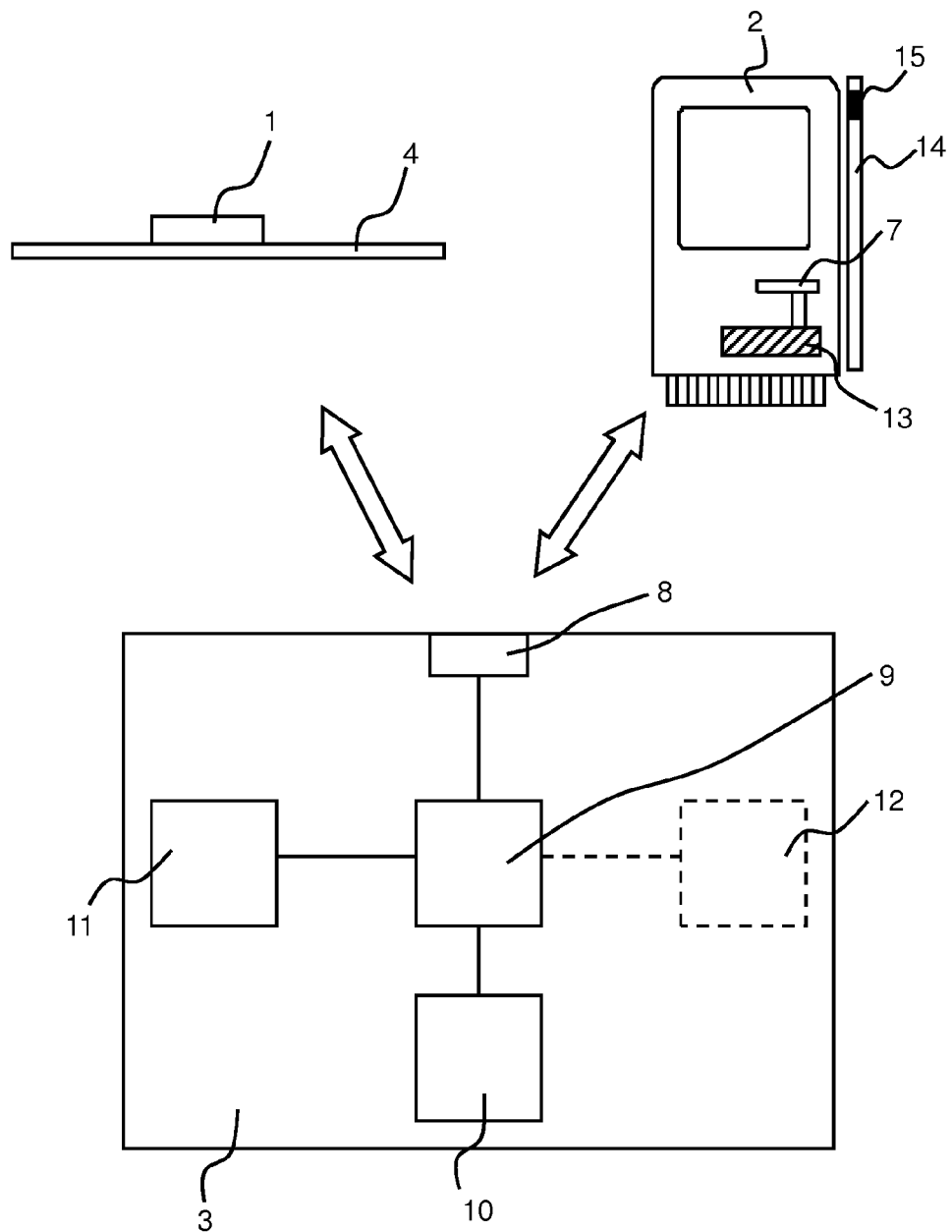
FIG. 3 illustrates a schematic representation of another medical system, the medical device being provided with a lancing device according to an embodiment of the present disclosure.

FIG. 3 shows a schematic representation of another medical system. In this embodiment, the medical device 2 can have a lancing device 14 which may be a separate detachable unit and may be referred to as an additional medical device. The lancing device 14 can puncture the skin of a patient. The lancing device 14 can have a further medical device storage element 15 separate from the medical device storage element 7.

In embodiment shown in FIG. 3, when checking the patient identity the further medical device storage element 15 can also read the patient identifying data stored in a way to that of the medical device storage element 7. The clearance signal may only be outputted by the clearing device 3 if clearance is detected for both the medical device 2 and the additional medical device 14. Separate/different signal outputs can also be used by the medical device 2 and the additional medical device 14 so that a clearance signal can be output for the medical device 2 but a warning or blocking signal can be output for the additional medical device 14 such as when the comparison of data on the further medical device storage element 15 with that on the patient storage element 1 did not reveal patient identity. Thus, the medical device 2, a blood sugar testing device for example, can be used for a blood sugar analysis for the identified patient whereby the additional medical device 14, a lancing device for example, may not be used.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A medical system, the medical system comprising:
a patient storage element, wherein the patient storage element is assigned to a patient by identification information identifying the patient;
a medical device, wherein the medical device is a lancing device for puncturing a patient's skin and comprises a contaminating patient application;
a medical device storage element, wherein the medical device storage element is provided on the medical device and comprises use information; and
a clearing device, wherein the clearing device receives the identification information from the patient storage element and the use information from the medical device storage element and analyzes the use information, and wherein if in analyzing the use information it is found that application of the medical device to the patient is allowed, a clearance signal is outputted; if in analyzing the use information it is found that application of the medical device to the patient is not allowed, the identification information is analyzed; and if in analyzing the identification information it is found that application of the medical device to the patient is allowed, a clearance signal is outputted.

2. The medical system according to claim 1, wherein the use information comprises disinfection information, information that the medical device was previously used on another patient, and/or information that the medical device has not been previously used for said contaminating patient application.

3. The medical system according to claim 1, wherein the clearing device is at least partially implemented as an integrated device with the patient storage element and the medical device storage element.

4. The medical system according to claim 1, wherein the patient storage element is a RFID storage element, a passive storage element, an active storage element or combinations thereof.

5. The medical system according to claim 1, wherein the medical device storage element is a RFID storage element, a passive storage element, an active storage element or combinations thereof.

6. The medical system according to claim 1, wherein the patient storage element is provided on a patient attachment element.

7. The medical system according to claim 1, wherein the medical device storage element is a disposable article detachably applied to the medical device.

8. The medical system according to claim 1, wherein the patient storage element is connected to a motion sensor.

9. The medical system according to claim 1, wherein the medical device storage element is connected to a motion sensor.

10. The medical system according to claim 1, wherein the clearing device comprises a detection element configured to start an operation mode in which the identification information and the use information are collected automatically by the clearing device from the patient storage element and the medical device storage element, respectively, if the patient storage element or the medical device storage element is detected by the detection element as being located in the vicinity of the medical device.

11. The medical system according to claim 1, wherein the clearing device is connected to an operation module of the medical device.

12. The medical system according to claim 11, wherein if in analyzing it is found that application of the medical device to the patient is allowed, the clearing device provides the clearance signal with an operation clearing signal, wherein the operation clearing signal is provided to the operation module for clearing use of an operation function of the medical device.

13. A method for operating a medical system, the method comprising:
- providing a patient storage element, wherein the patient storage element comprises identification information identifying a patient;
- providing a medical device storage element on a medical device, wherein the medical device is a lancing device for puncturing a patient's skin and comprises a contaminating patient application;
- providing use information on the medical device storage element; and
- providing a clearing device, wherein the clearing device receives the identification information from the patient storage element and the use information from the medical device storage element and analyzes the use information, and wherein if in analyzing the use information it is found that application of the medical device to the patient is allowed, a clearance signal is outputted; if in analyzing the use information it is found that application of the medical device to the patient is not allowed, the identification information is analyzed; and if in analyzing the identification information it is found that application of the medical device to the patient is allowed, a clearance signal is outputted.

* * * * *